United States Patent [19]

Gordon

[11] 4,053,490

[45] Oct. 11, 1977

[54] PROCESS FOR PRODUCTION OF AMMONIUM N⁴-ACETYSULFANILYLCYANAMIDE

[75] Inventor: John Edson Gordon, Martinsville, N.J.

[73] Assignee: American Cyanamid Company, Stamford, Conn.

[21] Appl. No.: 745,500

[22] Filed: Nov. 26, 1976

[51] Int. Cl.² .......................................... C07C 143/80
[52] U.S. Cl. ........................ 260/397.7 R; 260/551 C; 260/DIG. 6
[58] Field of Search ................... 260/397.7 R, 551 C, 260/DIG. 5, DIG. 6, 705

[56] References Cited

U.S. PATENT DOCUMENTS

| | | | |
|---|---|---|---|
| 2,259,721 | 10/1941 | Anderson et al. | 260/551 C X |
| 2,357,249 | 8/1944 | Anderson | 260/397.7 R |
| 2,463,793 | 3/1949 | Mosnier | 260/397.7 R |
| 3,461,143 | 8/1969 | Nargund | 260/397.7 R |
| 3,819,603 | 6/1974 | Shen et al. | 260/397.7 R X |

OTHER PUBLICATIONS

Rudnicki et al., CA 55:5426e (1961).
Winnek et al., JACS 64, pp. 1682–1685 (1942).

*Primary Examiner*—Daniel E. Wyman
*Assistant Examiner*—Thomas A. Waltz
*Attorney, Agent, or Firm*—Harry H. Kline

[57] ABSTRACT

There is provided a process for preparing highly pure, concentrated aqueous solutions of ammonium N⁴-acetylsulfanilylcyanamide from either an alkali or alkaline earth metal salt, or mixtures thereof, of N⁴-acetylsulfanilylcyanamide by liquid ion-exchange.

17 Claims, No Drawings

PROCESS FOR PRODUCTION OF AMMONIUM N⁴-ACETYSULFANILYLCYANAMIDE

The present invention relates to a process for the preparation of ammonium N⁴-acetylsulfanilylcyanamide in aqueous solution. More particularly, it relates to a process for the preparation of highly pure, concentrated aqueous solutions of ammonium N⁴-acetylsulfanilylcyanamide from either an alkali or alkaline earth metal salt, or mixtures thereof, of N⁴-acetylsulfanilylcyanamide by liquid ion-exchange.

Ammonium N⁴-acetylsulfanilylcyanamide, hereinafter termed AASC, can be rearranged to N⁴-acetylsulfaguanidine, hereinafter termed ASG, as described in U.S. Pat. No. 2,463,793. The latter can be hydrolyzed to sulfaguanidine hydrate, hereinafter termed SG, a chemotherapeutic agent useful in the treatment of various intestinal infections. The reactions are set forth below:

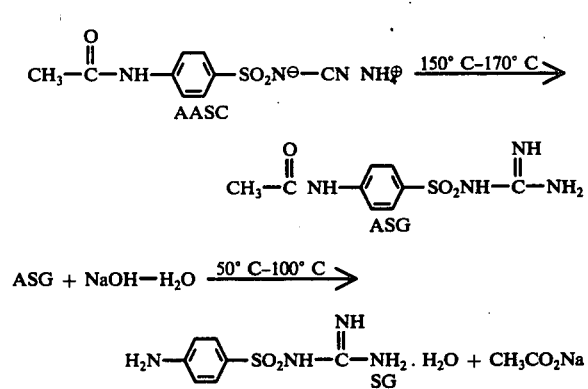

N⁴-acetylsulfanilylcyanamide and the anion thereof, hereinafter termed ASC and AS$\overline{C}$, respectively, are represented by the formulas below:

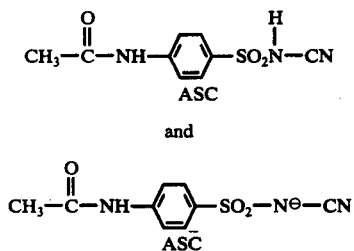

As far as is presently known, AASC is prepared by initially isolating the crystalline calcium salt of ASC and then reacting the latter with an aqueous solution of ammonium carbonate as disclosed in U.S. Pat. No. 2,463,793. After separating resultant calcium carbonate precipitate, the aqueous filtrate is concentrated under vacuum to obtain a solution containing at least 50%, by weight, of desired AASC.

There is, therefore, a present need to provide a process for the preparation of concentrated aqueous solutions of AASC which avoids the isolation of the calcium salt of ASC, the filtration of calcium carbonate, and the concentration of the aqueous filtrate. There is also a need to provide for a process which will yield concentrated aqueous solutions of AASC in high yields and purity.

It has been found that a highly pure, concentrated aqueous solution of AASC can be readily prepared in high yields and purity by a liquid ion exchange procedure which comprises the steps of: (1) vigorously contacting a substantially neutral aqueous mixture of an alkali or alkaline earth metal salt of ASC with an inorganic acid and a water-immiscible organic solution of a water-immiscible amine acid-binding extractant, the amounts of acid and acid-binding extractant being sufficient to extract substantially all of the ASC into the said organic solution; (2) separating the aqueous phase and vigorously contacting the organic phase with an amount of dilute aqueous alkali sufficient to remove acid contaminants therefrom, (3) separating the aqueous phase and vigorously contacting the organic phase with ammonium hydroxide, thereby forming AASC which is then counter-extracted into the aqueous phase; and, finally, (4) separating the aqueous phase to obtain a concentrated solution of AASC.

It has been further found that the present invention involves a process for the preparation of a highly pure, concentrated aqueous solution of ammonium N⁴-acetylsulfanilylin good yield which comprises:

a. vigorously contacting an essentially neutral aqueous mixture of an alkali or alkaline earth metal salt of N⁴-acetylsulfanilylcyanamide with an inorganic acid and a solution of a water-immiscible organic solvent containing a high molecular weight, aliphatic amine, acid-binding extractant to form a two-phase mixture consisting of an organic phase and an aqueous phase, the amount of said acid being at least equal to the number of moles of acid-binding sites in said amino extractant and the amount of said alkali or alkaline earth metal salt of N⁴-acetylsulfanilylcyanamide being sufficient to convert from about 70% to 100% of said acid-binding sites to an amine salt of N⁴-acetylsulfanilylcyanamide, b. separating the aqueous phase therefrom and vigorously contacting the organic phase with a dilute aqueous alkali in an amount essentially equal to the number of moles of acid-binding sites in said amine extractant not bound to N⁴-acetylsulfanilylcyanamide, c. separating the aqueous phase therefrom and vigorously contacting the organic phase with ammonium hydroxide in an amount substantially equal to the molecular equivalents of said alkali or alkaline earth metal salt of N⁴-acetylsulfanilylcyanamide used, and d. recovering the aqueous phase therefrom comprising ammonium N⁴-acetylsulfanilylcyanamide in good yield and purity.

In a preferred embodiment of the process of the invention, the water-immiscible organic solution containing the acid-binding extractant is first reacted with an aqueous inorganic acid to form a water-immiscible organic solution of a salt of said acid-binding extractant. Then, following separation of the aqueous phase, the organic phase is contacted with an aqueous solution of an alkali salt of ASC and processed, as described above, in the absence of an inorganic acid.

In the process of the invention, liquid ion exchange is employed. Such liquid ion exchange can be defined as a liquid extraction process which operates by the interchange of an ion at the interface between an aqueous phase and an organic phase containing a water-immiscible, acid-binding extractant. In general, the acid-binding extractant is a high molecular weight, aliphatic amine more specifically defined hereinbelow.

The liquid ion exchange process involves three reactions which are as follows:

1. The extractant is converted to an amine salt. As shown the secondary amine is converted to its halide salt.

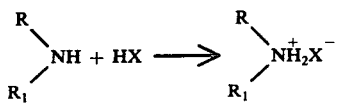

where R and $R_1$ each represent a higher alkyl radical of from 8 to 18 carbon atoms and X is halogen, such as chloro, bromo or iodo;

2. The anion of the amine salt is exchanged for the anion of ASC, (i.e., SASC) as shown below, where SASC represents the sodium salt of ASC:

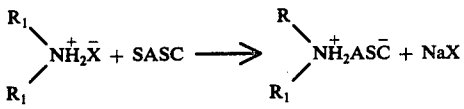

where R, $R_1$, and X are as defined above, and

3. The ASC̄ is removed from the acid-binding extractant with ammonium hydroxide and counter-extracted into the aqueous phase to obtain a concentrated aqueous solution of AASC, as shown below:

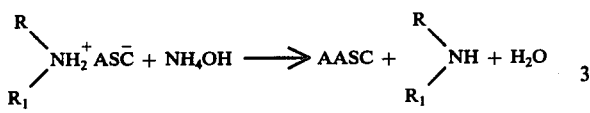

where $R_1$ and $R_2$ are as defined above.

Advantageously, an aqueous solution of SASC can be readily prepared by reacting acetylsulfanilyl chloride with cyanamide at about 20° C. to 35° C. in the presence of preferred caustic soda, as shown below:

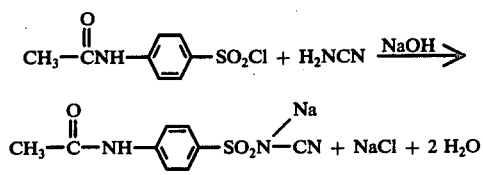

As described above, other illustrative alkali metal or alkaline earth metal salts, such as the potassium, lithium, barium, calcium, and magnesium, of ASC can be prepared in a similar manner by using equivalent amounts of potassium, lithium, barium, calcium, and magnesium hydroxide, respectively. In the cases of barium, calcium, and magnesium hydroxide aqueous dispersions are obtained.

In conducting the process of the invention, a solution of an amine acid-binding extractant is prepared in a water-immiscible organic solvent. Preferably, the solution contains a solubilizing amount of a higher alcohol. More specifically, the solution is a mixture which comprises from about 8% to 10%, by weight, of a $C_6 - C_{12}$ alcohol, from about 20% to 25%, by weight, of an amine acid-binding extractant, and from about 72% to 65%, by weight, of a water-immiscible organic solvent.

Exemplary higher alcohols include aliphatic alcohols, such as n-hexyl alcohol, n-heptyl alcohol, n-octyl alcohol, 2-ethylhexyl alcohol, n-dodecyl alcohol, and the like, the preferred higher alcohol being n-hexyl alcohol.

Illustrative acid-binding extractants include high molecular weight, aliphatic amines, such as tri-n-octylamine, tri-i-octylamine, tri-n-decylamine, methyl-di-i-octylamine, and the like. Preferably, the acid-binding extractant is a long-chain, high molecular weight secondary aliphatic amine such as Amberlite® LA-1, or LA-2, (Rohm and Haas Company, Philadelphia, Pa.), the latter having an acid-binding capacity of 2.5 –2.7 and 2.6 –2.8 milliequivalents per gram, respectively.

Suitable water-immiscible organic solvents include benzene, toluene, o-xylene, chlorobenzene, o-dichlorobenzene, chloroform, and the like; the preferred organic solvent being toluene.

Advantageously, the amine extractant can be converted to an amine salt and exchanged with ASC̄ in a single step by vigorously contacting the organic solution thereof with a neutral aqueous mixture of an alkali or alkaline earth metal salt of ASC, or a mixture of said metal salts in a suitable phase separation vessel and adding a suitable acid, or mixture of acids thereto. The alkali or alkaline earth metal salt of ASC can be used either in the form of an aqueous solution or dispersion provided that the pH of the solution or dispersion is adjusted to about 7 prior to use.

Suitable inorganic acids include hydrochloric, sulfuric, nitric, hydrobromic, and the like. The preferred acid is hydrochloric acid. Organic acids such as formic, azelaic, and the like, can also be employed in the process of the invention.

In general, the amount of acid employed in the process of the invention can range from about 1.00 to 1.20, and preferably about 1.10 to 1.15, molecular equivalents per molecular equivalent of amine extractant. The amount of said metal salt, or mixture of metal salts, of ASC used can range from about 0.7 to 1.0, and preferably from about 0.75 to 0.80, molecular equivalent per molecular equivalent of amine extractant. After vigorously contacting these materials at ambient temperatures for from about five to thirty minutes, the two-phase mixture is allowed to stand until complete separation of the phases occurs, and the aqueous phase is separated. Titration of the recovered aqueous phase shows that about 99.0% to 99.5% of the ASC̄ has been extracted into the organic phase.

The residual organic phase, containing ASC̄ bound to amine acid-binding extractant, preferably at about 75% to 80% of amino sites, is vigorously contacted for about 5 to 30 minutes with an amount of dilute aqueous alkali molecularly equivalent to any acid contaminants present therein, as determined analytically. Resultant two-phase mixture is allowed to stand until complete separation of the phases occurs and the aqueous phase is separated by means of a hydro.

Residual organic solution is contacted at ambient conditions with about 1.0 to 1.5, molecular equivalents of ammonium hydroxide per molecular equivalent of metal salt of ASC charged initially. The two-phase mixture is then allowed to stand until the separation of the phases is complete, and the aqueous phase is separated to recover a solution containing about 50% to 60% AASC essentially free of ammonium acetylsulfanilate and other ammonium salts, such as ammonium chloride. The overall yield based on the alkali metal salt of ASC is about 96 to 98% of theoretical.

Alternatively, and optionally, a second extraction with ammonium hydroxide can be carried out to insure complete removal of ASC̄ from the organic phase. The organic phase can be contacted with acid and then recycled.

The following examples are merely illustrative of the process of this invention. Unless otherwise noted, all parts and percentages are by weight.

EXAMPLE 1

Preparation of Aqueous Mixtures of SASC

A solution is prepared by adding 21.45 grams of 50%, by weight, aqueous cyanamide (10.725 grams real; 0.255 mole) to 100 mls. of water. A mixture of 14 grams of water and 56.7 grams of N-acetylsulfanilyl chloride (0.243 mole), and 38.91 grams of 50% aqueous caustic soda (19.45 grams real; 0.486 mole) are simultaneously added to the aqueous solution of cyanamide over about 2 hours while maintaining the pH of the reaction mixture at about 9.0 to 9.5 and the temperature at about 25°–30° C. After the additions are completed the reaction mixture is stirred for an additional hour while the pH is maintained at 9.0 to 9.5. There are obtained 232 grams of aqueous solution containing 26.77%, by weight of SASC, amounting to a yield of 98% of theoretical.

In a manner as described in Example 1, 248 grams of an aqueous solution containing 26.62% by weight of potassium $N^4$-acetylsulfanilylcyanamide (KASC) is similarly prepared by substituting 54.57 grams of 50% aqueous potassium hydroxide for the caustic soda. The yield obtained is 98% of theoretical.

EXAMPLE 2

A solution of the hydrochloride salt of the acid-binding extractant is prepared by mixing 96.6 grams of Amberlite ® LA-1 (0.261 mole) with 38.6 grams of n-hexyl alcohol and 347.8 grams of toluene to provide a solution comprising 20% by weight Amberlite ® LA-1, 8% by weight n-hexyl alcohol and 72%, by weight, toluene. The organic solution is then vigorously shaken with 76.2 grams of 14% aqueous hydrochloric acid (0.292 mole) for five minutes at ambient conditions and allowed to stand in a suitable separatory funnel until the separation of the phases is complete. The aqueous phase is then separated.

196 Grams of a 26.8% aqueous solution of SASC (0.201 mole) is adjusted to pH 7 by adding dilute hydrochloric acid thereto and added to the separatory funnel containing the residual organic phase. The mole ratio of SASC added to the acid-binding extractant is 0.77. The two-phase mixture is vigorously shaken at ambient conditions for 10 minutes and allowed to stand until the separation of the phases is complete. The aqueous phase which is separated leaves an organic solution containing essentially a mixture of the $N^4$-acetylsulfanilylcyanamide and hydrochloride salts of the extractant.

The solution of the acid-binding extractant is vigorously shaken with 20 grams of 14% aqueous sodium hydroxide (0.061 mole) for 10 minutes and allowed to stand until the separation of the phases is complete. The aqueous phase containing sodium chloride and sodium acetylsulfanilate is separated therefrom.

The residual organic phase, now containing substantially $AS\overline{C}$ bound to the acid-binding extractant, is vigorously shaken for 10 minutes with about 27 grams of 14% aqueous ammonia to remove the $AS\overline{C}$ from the acid-binding extractant, as AASC, into the aqueous phase. The two-phase mixture is allowed to stand until the phases are completely separated and the aqueous phase is separated to obtain 106 grams of solution containing 50.5 grams of AASC, 98% of theoretical.

EXAMPLE 3

The procedure of Example 2 is used in every respect except that 217.5 grams of 26.62% KASC (0.209 mole) previously adjusted to pH 7, is used instead of SASC, and 93.1 grams of Amberlite ® LA-2 (0.251 mole) is employed instead of Amberlite ® LA-1.

The solution of acid-binding reactant salt, namely, about 80% loaded with $AS\overline{C}$ by anion-exchange with KASC, is vigorously shaken with 17.4 grams of 14% aqueous sodium hydroxide (0.05 mole) and processed in a manner as described in Example 2 to obtain AASC. Similar results are obtained.

EXAMPLE 4

A solution is prepared by mixing 98.5 grams of Amberlite ® LA-1 (0.266 mole) with 40.00 of n-hexyl alcohol and 3-44.5 grams of toluene. The solution is added to a separatory funnel, followed by the addition thereto of 226.4 grams of 26.8% aqueous solution of SASC (0.232 mole) having a pH of 7 and 58.6 mls. of 4.5 molar hydrochloric acid (0.266 mole). The two-phase mixture is vigorously shaken for 12 minutes and allowed to stand until the separation of the phases is complete. The aqueous phase is then separated and the residual organic phase is vigorously shaken with 9.7 grams of 14% aqueous sodium hydroxide (0.034 mole). The two-phase mixture is allowed to stand until the separation of the phases is attained and the aqueous phase is separated therefrom.

The residual organic phase is vigorously shaken with 31.0 grams of 14% aqueous ammonia (0.255 mole) for 10 minutes and allowed to stand until the separation of the phases is complete. The aqueous phase is separated and the organic phase is extracted again with 5 grams of 14% aqueous ammonia. The two phases are allowed to settle and the aqueous phase is separated and combined with the first aqueous ammonia extract to obtain 94.0 grams containing 61.7% by weight of AASC. The yield is 97.6% of theoretical.

EXAMPLE 5

Commercial calcium cyanamide (22.9 grams real; 0.286 mole) is stirred with 70 mls. of water at 25° to 27° C for 2 hours and filtered. To the filtrate 55.85 grams of acetylsulfanilyl chloride (0.239 mole) is gradually added at 25°–35° C over a period of 45 minutes while keeping the solution alkaline by adding 40% sodium hydroxide as necessary. The calcium salt of $N^4$-acetylsulfanilylcyanamide precipitates slowly. The resulting slurry is stirred for 2 hours at room temperature and then adjusted to pH 7 with hydrochloric acid.

A solution of acid-binding extractant is prepared by mixing 98.5 grams of Amberlite ® LA-1 (0.266 mole) with 40.0 grams of n-hexyl alcohol and 344.5 grams of toluene. The solution is added to a separatory funnel followed by the addition thereto of the slurry containing calcium $N^4$-acetylsulfanilycyanamide and 58.6 mls. of 4.54 molar hydrochloric acid (0.266 mole). The two-phase mixture is vigorously shaken for 20 minutes and allowed to stand until the separation of the phases is complete. The aqueous phase is then separated and the residual organic phase is processed as in Example 4 with 14% aqueous sodium hydroxide and aqueous ammonia to obtain a concentrated solution of AASC. The yield is 94% of theoretical.

In the manner as described above, a concentrated solution of AASC is obtained by substituting barium cyanamide (50.7 grams real; 0.286 mole) for the calcium cyanamide. Similar results are obtained.

EXAMPLE 6

The combined aqueous ammonia extracts from Example 4 on evaporation in an open dish at 70° to 80° C for about fifteen hours and drying at 100° to 105° C for 6 hours yield 58.0 grams of large, glassy crystals of AASC hydrate. A sample (2 grams) of the glassy crystals is placed in a test tube and heated in an oil bath at 171.5° to 172° C for 30 minutes. The sample is then cooled to ambient conditions. The infrared absorption spectrum of the product resembles that of $N^4$-acetylsulfanilylguanidine.

I claim:
1. A process for the preparation of a highly pure, concentrated aqueous solution of ammonium $N^4$-acetylsulfanilylcyanamide in good yield which comprises:
  a. vigorously contacting an essentially neutral aqueous mixture of an alkali or alkaline earth metal salt or mixtures thereof of $N^4$-acetylsulfanilylcyanamide with an inorganic acid and a solution of a water-immiscible organic solvent containing a high molecular weight, aliphatic amine, acid-binding extractant to form a two-phase mixture consisting of an organic phase and an aqueous phase, the amount of said acid being at least equal to the number of moles of acid-binding sites in said amino extractant and the amount of said alkali or alkaline earth metal salt of $N^4$-acetylsulfanilylcyanamide being sufficient to convert from about 70% to 100% of said acid-binding sites to an amine salt of $N^4$-acetylsulfanilylcyanamide,
  b. separating the aqueous phase therefrom and vigorously contacting the organic phase with a dilute aqueous alkali in an amount essentially equal to the number of moles of acid-binding sites in said amine extractant not bound to $N^4$-acetylsulfanilylcyanamide,
  c. separating the aqueous phase therefrom and vigorously contacting the organic phase with ammonium hydroxide in an amount substantially equal to the molecular equivalents of said alkali or alkaline earth metal salt of $N^4$-acetylsulfanilylcyanamide used, and
  d. recovering the aqueous phase therefrom comprising ammonium $N^4$-acetylsulfanilylcyanamide in good yield and purity.
2. A process according to claim 1 wherein said neutral aqueous mixture is a solution of sodium $N^4$-acetylsulfanilylcyanamide.
3. A process according to claim 1 wherein said neutral aqueous mixture is a solution of potassium $N^4$-acetylsulfanilylcyanamide.
4. A process according to claim 1 wherein said aqueous mixture is a dispersion of calcium $N^4$-acetylsulfanilylcyanamide.
5. A process according to claim 1 wherein said aqueous mixture is a dispersion of magnesium $N^4$-acetylsulfanilylcyanamide.
6. A process according to claim 1 wherein said aqueous mixture is a dispersion of barium $N^4$-acetylsulfanilylcyanamide.
7. A process according to claim 1 wherein said solution of water-immiscible organic solvent and aliphatic amine acid-binding extractant additionally contains a solubilizing amount of an aliphatic alcohol of from 6 to 12 carbon atoms.
8. A process according to claim 7 wherein said water-immiscible solution comprises about 20% to 25%, by weight, of aliphatic amine acid-binding extractant, about 8 to 10%, by weight, of n-hexyl alcohol, and about 72% to 65%, by weight, of toluene.
9. A process according to claim 8 wherein said aliphatic amine acid-binding extractant is a secondary amine having an acid-binding capacity of 2.5 to 2.8 milliequivalents per gram.
10. A process for the preparation of a highly pure, concentrated aqueous solution of ammonium $N^4$-acetylsulfanilycyanamide which comprises:
  a. vigorously contacting a solution of a water-immiscible organic solvent containing a long-chain, high molecular weight, aliphatic amine acid-binding extractant, with a dilute aqueous solution of an inorganic acid to form a two-phase mixture consisting of an organic phase and an aqueous phase, the amount of said acid being at least equal to the number of moles of acid-binding sites in said amine extractant,
  b. separating the aqueous phase and vigorously contacting the organic phase with an substantially neutral aqueous solution of an alkali metal salt of $N^4$-acetylsulfanilylcyanamide, the amount of said alkali metal salt being sufficient to convert about 70% to 100% of said acid-binding sites to an amine salt of $N^4$-acetylsulfanilycyanamide,
  c. separating the aqueous phase therefrom and vigorously contacting the organic phase with a dilute aqueous alkali in an amount substantially equal to the number of moles of acid-binding sites in said amine extractant not bound to $N^4$-acetylsulfanilylcyanamide, and
  d. separating the aqueous phase therefrom and vigorously contacting the organic phase with ammonium hydroxide in an amount essentially equal to the moles of said alkali metal salt of $N^4$-acetylsulfanilylcyanamide used, and recovering the aqueous phase therefrom.
11. A process according to claim 10 wherein said alkali metal salt is sodium $N^4$-acetylsulfanilylcyanamide.
12. A process according to claim 10 wherein said alkali metal salt is potassium $N^4$-acetylsulfanilylcyanamide.
13. A process according to claim 10 wherein said acid is hydrochloric acid.
14. A process according to claim 10 wherein said dilute alkali is dilute caustic soda.
15. A process according to claim 10 wherein said solution of water-immiscible organic solvent and aliphatic amine acid-binding extractant additionally contains a solubilizing amount of an aliphatic alcohol of 6 to 12 carbon atoms.
16. A process according to claim 15 wherein said water-immiscible solution comprises about 20% to 25%, by weight of an aliphatic amine acid-binding extractant, about 8% to 10%, by weight, of n-hexyl alcohol, and about 72% to 65%, by weight, of toluene.
17. A process according to claim 16 wherein said aliphatic amine acid-binding extractant is a secondary amine having an acid-binding capacity of 2.5 to 2.8 milliequivalents per gram.

* * * * *